United States Patent [19]

Kluger et al.

[11] 4,352,921
[45] Oct. 5, 1982

[54] AMINOALKOXYHEXANES AND EPOXY RESIN COMPOSITIONS CONTAINING THEM

[75] Inventors: Edward W. Kluger, Pauline; Calvin D. Welch, Spartanburg, both of S.C.

[73] Assignee: Milliken Research Corporation, Spartanburg, S.C.

[21] Appl. No.: 230,723

[22] Filed: Feb. 2, 1981

[51] Int. Cl.³ .............................................. C08G 59/50
[52] U.S. Cl. ..................................... 528/111; 528/407; 564/491; 564/493; 564/504; 564/507
[58] Field of Search ................. 528/111, 407; 564/504, 564/507, 491, 493

[56] References Cited

U.S. PATENT DOCUMENTS

| 3,306,809 | 2/1967 | Williamson et al. | 528/111 X |
| 3,316,185 | 4/1967 | Reinking | 564/504 X |
| 3,799,986 | 3/1974 | Poppelsdorf | 564/504 X |

FOREIGN PATENT DOCUMENTS 581994 10/1946 United Kingdom .

OTHER PUBLICATIONS

Lee & Neville, *Handbook of Epoxy Resins*, McGraw-Hill, N.Y., 1967, pp. 1-2.

Primary Examiner—Earl A. Nielsen
Attorney, Agent, or Firm—H. William Petry; Terry T. Moyer

[57] ABSTRACT

Aminoalkoxyhexane compounds are provided having the following formula:

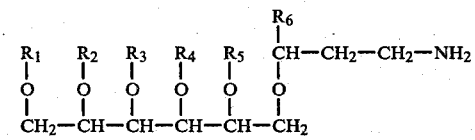

wherein $R_1$, $R_2$, $R_3$, $R_4$, and $R_5$ are independently selected from H and

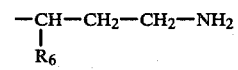

wherein $R_6$ is selected from H and a lower alkyl group having from 1 to about 4 carbon atoms.

9 Claims, No Drawings

AMINOALKOXYHEXANES AND EPOXY RESIN COMPOSITIONS CONTAINING THEM

The present invention relates to aminoalkoxyhexane compounds, and to methods for curing epoxy resins wherein aminoalkoxyhexane compounds are employed as a curing agent. The present invention also relates to epoxy resin compositions containing aminoalkoxyhexane compounds as epoxy curing agents.

Epoxy resins were first introduced commercially in the United States in about 1950, and since then their use has grown rapidly. Epoxy resins may be broadly defined as resinous intermediate materials which are characterized by the presence of the epoxy group

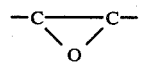

In general, epoxy resins are not used by themselves but rather they require the addition of a curing agent or hardener to convert them into a thermoset material. Epoxy resins have gained wide acceptance in structural applications and in protective coatings because of their generally excellent toughness, adhesion, chemical resistance, and electrical properties. The combination of these properties is generally not found in any other single plastic material.

A relatively large number of chemical reagents are available or known to have utility as curing agents or hardeners which may be added to epoxy resins to convert them to thermoset materials. It is also known that in the curing process both the epoxy and the hydroxyl groups of the resin may be involved. Curing agents are available whereby curing may be accomplished at room temperature or upon heating. Curing may take place in general either by a coupling or addition process, or by catalytic polymerization.

The known curing agents or hardeners for epoxy resins fall into three categories: (1) the acidic type, e.g., acid anhydrides; (2) aldehyde condensation products, e.g., phenol-, urea-, and melamine-formaldehyde resins; and (3) amine type, e.g., aliphatic and aromatic amines, polyamides, tertiary amines, and amine adducts. The novel aminoalkoxyhexane compounds of the present invention may be employed as the third type, namely the amine type, of epoxy curing agent.

The aminoalkoxyhexane compounds of the present invention may be represented by the following structural formula:

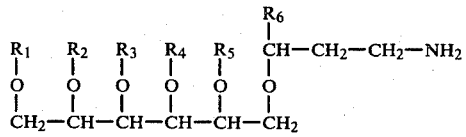

wherein $R_1$, $R_2$, $R_3$, $R_4$, and $R_5$ are independently selected from H and

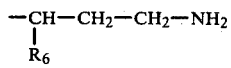

wherein $R_6$ is selected from H and a lower alkyl group having from 1 to about 4 carbon atoms. Preferably in the above structural formula all of the available hydroxyl groups are reacted so that $R_1$, $R_2$, $R_3$, $R_4$ and $R_5$ are all

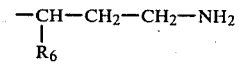

and $R_6$ has the value mentioned above. Even more preferably such reaction is accomplished by means of acrylonitrile which is subsequently reduced so that $R_6$ is H.

The present invention also relates to the use of such compounds as epoxy curing agents and to epoxy resin compositions which contain 100 parts by weight of at least one epoxy resin and from about 15 parts to about 50 parts, preferably about 20 parts to about 30 parts by weight of the aminoalkoxyhexane compounds of the invention. Such cured products have good flexibility, high heat distortion temperatures and excellent solvent resistance.

The aminoalkoxyhexanes of the present invention may be prepared by a two step process. In a first step, a suitable ethylenically unsaturated nitrile, e.g., acrylonitrile, crotonitrile, or methacrylonitrile may be reacted with sorbitol under conventional reaction conditions in the presence of a conventional cyanoethylation catalyst such as sodium hydroxide, potassium hydroxide or lithium hydroxide. In this first step one, several or all of the free hydroxyl groups may be cyanoalkylated to provide a cyanoalkylated intermediate. The preferred unsaturated nitrile for use in the cyanoalkylation is acrylonitrile, and preferably all of the available hydroxyl groups of the sorbitol are cyanoalkylated. According to such preferred embodiment the intermediate compound which is provided is 1,2,3,4,5,6-hexa-2-cyanoethoxyhexane. For convenience the details of the invention will be described with particular reference to acrylonitrile as the cyanoalkylation agent and to 1,2,3,4,5,6-hexa-2-cyanoethoxyhexane as the cyanoalkylated intermediate.

The second step in the preparation of the novel compounds of the invention is the hydrogenation of the cyanoalkyl groups of the cyanoalkylated intermediate, e.g., 1,2,3,4,5,6-hexa-2-cyanoethoxyhexane. Such reduction may be accomplished with hydrogen and ammonia either in the presence or absence of a solvent and a metal catalyst. The corresponding hexamine may be produced in high yields as shown in the equation below:

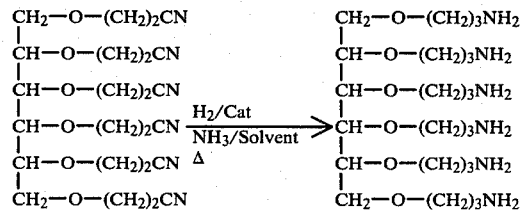

The temperature at which the above described reduction of hexanitrile may be carried out can vary widely. However, generally the temperature may be within a range of from about 30°–150° C. and preferably in the range of 80°–125° C. Likewise, the period of time required for the reaction to go to substantial completion can vary widely, such being dependent on the hydrogen pressure and the particular catalyst employed as well as the temperature at which such reaction is carried out. Generally, however, the reaction proceeds to completion when the reactants are contacted at the required temperature for a period of time from about 0.5 to about 4 hours. Pressures in the range of about 1000 to about 5000 psi can be used to accomplish the reduction. While pressure in the higher range (2100–5000 psi) can be used and may be advantageous, the preferable range of pressure is 1000–2000 psi. The use of ammonia in this reduction is a critical factor in the process to maintain high yields of the corresponding hexamine. The presence of ammonia serves to inhibit formation of secondary amines. The amount of ammonia used can vary from 5 moles of ammonia per mole of hexanitrile to 30 moles per mole of hexanitrile. Preferably 12 to about 20 moles of ammonia are used per mole of hexanitrile.

The hydrogenation of the hexanitrile can be carried out in the presence or absence of a solvent. When solvent is employed, any suitable solvent which will not interfere with the desired hydrogenation can be employed, such as cycloaliphatic ethers, e.g., dioxane, tetrahydrofuran, and the like, and higher boiling hydrocarbons, e.g., hexane, cyclohexane, heptane, decane, toluene, xylenes, and the like, and alcohols, e.g., methyl alcohol, ethyl alcohol, isopropyl alcohol, isobutyl alcohol and the like.

In carrying out the reduction of the hexanitrile any suitable reduction catalyst can be employed. Typical of such reduction catalysts are raney nickel, cobalt, palladium, platinum, ruthenium, rhodium, osmium, iridium, iron, including salts and oxides thereof and the like. Further, such catalysts can be in their free metal state or extended on a support such as charcoal, aluninum, kieselguhr and the like.

The amount of catalyst employed in the reduction can vary widely. However, generally the amount of catalyst will vary from about 1 to 30 weight percent, preferably from about 5 to 10 weight percent.

The process of reducing the hexanitrile has been described as a batch operation carried out in a high pressure stirred autoclave. However, other reducing modes will give equally good results. A continuous flow reactor may be used with suspended or fixed bed solid catalyst operating at the proper temperature, pressure, and flow rate to give the desired reduction. Alternatively, the desired reduction can be accomplished by incremental addition of the hexanitrile to a batch type reactor at the proper described operating conditions.

One particularly important use for the novel compounds of the present invention is their use as epoxy curing agents for polyepoxides. The polyepoxides which can be cured at elevated temperatures using the amino compounds as herein described are those polyepoxides possessing at least two

groups. These groups may be terminal, i.e.,

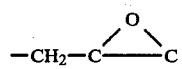

groups, or they may be in an internal position. However, especially desirable results can be obtained when the epoxy groups are terminal. The polyepoxides may be saturated or unsaturated, aliphatic, cycloaliphatic, aromatic or heterocyclic, and may be substituted such as with hydroxyl groups, ether radicals and the like. Further, the polyepoxides can be monomeric or polymeric. Such polyepoxides, and their preparation, are well known in the art.

The curing of the polyepoxides with the above-described amino compound curing agents of the present invention may be accomplished by simply mixing the two components together. While the reaction between the two components may occur slowly at room temperature, improved results can be obtained if the mixture is heated to a temperature of from about 50° C. to about 280° C. for a period of time of from about 1 to about 12 hours and thereafter post-curing the reaction product for an additional period of time from about 1 to about 8 hours at a temperature of from about 140° C. to about 225° C. With a small casting, curing of the reaction mixture can be obtained by heating the reaction mixture for about 2 hours at a temperature of from about 80° C. to about 100° C. and thereafter post-curing the reaction product at a temperature of from about 140° C. to about 225° C. for an additional 2 hours or so.

In curing polyepoxides it is generally desirable that the polyepoxide be in a mobile condition when the curing agent is added to ensure uniform mixing. If the polyepoxide is extremely viscous or solid at room or casting temperature, the polyepoxide may be heated to reduce the viscosity or a volatile liquid solvent which can escape from the polyepoxide composition containing the novel amino compound curing agent by evaporation before and/or during the curing of such polyepoxide composition can be added to the polyepoxide to reduce its viscosity. Typical of such volatile liquid solvents are ketones, such as acetone, methyl ethyl ketone and the like, ethers, such as ethyl acetate, butyl acetate and the like, ether alcohols, such as methyl, ethyl or butyl ethers of ethylene glycol and chlorinated hydrocarbons, such as chloroform.

In addition to the use of the amino compounds of the present invention as epoxy curing agents, many other uses can readily be envisioned by those skilled in the art. Thus, not only do the compounds of the present invention find utility as epoxy curing agents but such compositions can be employed as oil and fuel adductive intermediates. Further, the polyamines may be employed for the formation of diisocyanate compositions for the incorporation into polyurethane compositions, and the compound may be further reacted to form novel and useful polyamides.

In order to more fully describe the preparation and use of the novel compounds of the present invention the following examples are given. However, such examples are presented for illustration only and are not to be construed as unduly limiting the scope of the present invention. Unless otherwise indicated, all parts and/or percentages given in these examples are by weight.

EXAMPLE 1

In a 5000 cc three necked flask equipped with an overhead stirrer, reflux condenser, nitrogen purge, dropping funnel and thermometer was charged 185 ml of water, 10 gm of anhydrous lithium hydroxide, and 448.8 gm of sorbitol. The overhead stirrer was then adjusted to high speed and the reaction contents were preheated to 42° C. with a water bath. An additional 392.7 gm of sorbitol was added to the reaction flask with the water bath being maintained above 39° C.

Acrylonitrile was then added through the dropping funnel. Over the course of 2 hours a total of 1000 cc of acrylonitrile was added and the reaction temperature reached a maximum of 51° C. with the water bath being maintained above 39° C. An additional 320 gm of sorbitol was added to the reaction flask for a total of 6.38 moles as the reaction temperature dropped to 42° C. (the bath temperature was maintained at ~41°-43° C.). The remaining 1900 cc of acrylonitrile was then added over 2½ hours keeping the reaction temperature below 60° C. and the bath temperature above 38° C. A total of 2900 cc (44.1 moles) of acrylonitrile was added. The reaction flask was then post heated at 50°-55° C. for an additional 4 hours. The reaction contents were cooled to room temperature and neutralized with 25 ml of glacial acetic acid. The reaction contents were then reheated to 50° C. and filtered. The crude filtered reaction product was stripped of all excess volatiles such as acrylonitrile and water under vacuum (15–30 mmHg) and at a temperature not exceeding 60° C. to give 3242.9 gm of viscous 1,2,3,4,5,6-hexa-2-cyanoethoxyhexane. This hexanitrile was suitable for use without further purification.

EXAMPLE 2

In a two liter stirred autoclave was charged 167 gm of tetrahydrofuran (THF), 647 gm of a 36.5% weight 1,2,3,4,5,6-hexa-2-cyanoethoxyhexane-THF solution and 24 gm of 5 percent ruthenium on alumina. The autoclave was sealed and pressure checked to 2000 psi with hydrogen for leaks. Afterwards, 153 gm of liquid ammonia was charged. The pressure was then adjusted to 400 psi with hydrogen gas and the autoclave was heated to 125°-130° C. where a pressure of 1650-1700 psi developed. Samples were pulled from the autoclave and analyzed until the reaction was near completion. After three hours at 125°-130° C., the reaction was post heated at 145°-150° C. for an additional 30 minutes. The autoclave was then cooled and the contents were emptied. The excess ammonia, THF, and any n-propylamine were removed from the product under vacuum (15-30 mmHg) to give a colorless liquid. This colorless liquid was stripped further under higher vacuum (0.5 to 2.0 mmHg) to remove any reduced dicyanoethylated water impurity present. An IR spectrum of the final stripped 1,2,3,4,5,6-hexa-3-aminopropoxyhexane indicated that all the nitrile groups had been reduced. A potentiometric titration of the product with one normal hydrochloric acid resulted in a neutralization equivalent of 10.70 milliequivalents of HCl per one gram of product. The theoretical value for 1,2,3,4,5,6-hexa-3-aminopropoxyhexane (mwt=524.17 g/mole) was calculated to be 11.44 milliequivalents of HCl per gram of hexamine which is in good agreement with the observed experimental value.

EXAMPLE 3

In a two liter stirred autoclave was charged 200 gm of THF, 870 gm of a 36.5 percent weight 1,2,3,4,5,6-hexa-2-cyanoethoxyhexane-THF solution and 32 gm of 5 percent ruthenium on alumina. The autoclave was sealed and pressure checked to 2000 psi with hydrogen for leaks. Afterwards, 200 gm of liquid ammonia was charged. The pressure was then adjusted to 400 psi with hydrogen gas and the autoclave was heated to 125°-130° C. where a pressure of 1600-1650 psi developed. Samples were pulled from the autoclave and analyzed until the the reaction was near completion. After three hours at 125°-130° C., the reaction was post heated at 145°-150° C. for an additional 30 minutes. The autoclave was then cooled and the contents were emptied. The excess ammonia, THF and any n-propylamine were removed from the product under vacuum (15–30 mmHg) to give a colorless liquid. This colorless liquid was stripped further under higher vacuum (0.5 to 2.0 mmHg) to remove any reduced dicyanoethylated water impurity present. An IR spectrum of the final stripped hexamine indicated that all the nitrile groups had been reduced. A potentiometer titration of the product with one normal hydrochloric acid resulted in a neutralization equivalent of 10.60 milliequivalents of HCl per one gram of product (theoretical value 11.44 milliequivalents per gm).

EXAMPLE 4

To four beakers each containing 100 parts of epoxy resin based on diglycidyl ether of bisphenol A (n=0.2, WPE=185-195) were added the corresponding

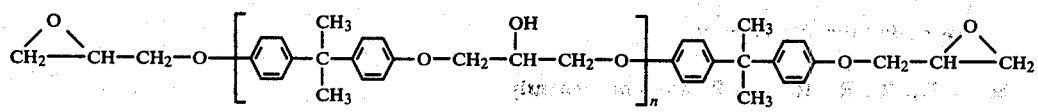

parts of 1,2,3,4,5,6-hexa-3-aminopropoxyhexane prepared in Example 2: 24.8 parts, 25.3 parts, 25.8 parts, and 26.3 parts. After mixing each beaker thoroughly for 2 minutes and centrifuging at a speed of 3000 rpm, these resin mixtures were placed in an aluminum mold and were cured for 2 hours at 80° C. and for another 2 hours at 150° C. The crosslinked products had glass transition temperatures measured with a differential scanning calorimeter (Perkin Elmer Model DSC-2) as are summarized in the table below.

| GLASS TRANSITION TEMPERATURE FOR 1,2,3,4,5,6-HEXA-3-AMINOPROPOXYHEXANE | | |
|---|---|---|
| ENTRY | PHR | TG(°C.) |
| 1 | 24.8 | 137.5 |
| 2 | 25.3 | 139.0 |
| 3 | 25.8 | 138.5 |
| 4 | 26.3 | 137.5 |

What is claimed is:

1. Aminoalkoxyhexane compounds having the following formula:

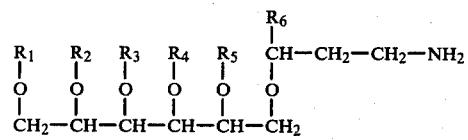

wherein $R_1$, $R_2$, $R_3$, $R_4$, and $R_5$ are independently selected from H and

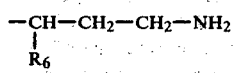

wherein $R_6$ is selected from H and a lower alkyl group having from 1 to about 4 carbon atoms.

2. The aminoalkoxyhexane compounds of claim 1, wherein $R_1$, $R_2$, $R_3$, $R_4$, and $R_5$ are

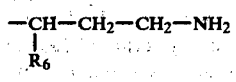

3. The aminoalkoxyhexane compounds of claim 2, wherein $R_6$ is H.

4. An epoxy resin composition comprising an epoxy resin and at least one epoxy resin curing agent of the formula:

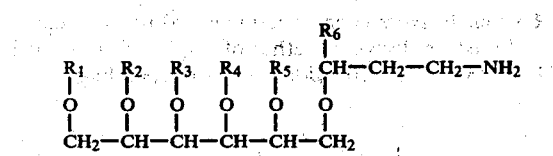

wherein $R_1$, $R_2$, $R_3$, $R_4$, and $R_5$ are independently selected from H and

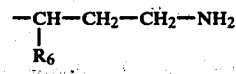

wherein $R_6$ is selected from H and a lower alkyl group having from 1 to about 4 carbon atoms.

5. The epoxy resin composition of claim 4, wherein said

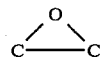

groups are terminal groups.

6. The epoxy resin composition of claim 5, wherein said epoxy resin is a diglycidyl ether of bis-phenol.

7. The epoxy resin composition of claim 4, wherein said epoxy resin curing agent is represented by the formula set forth in claim 4 and wherein $R_1$, $R_2$, $R_3$, $R_4$, and $R_5$ are

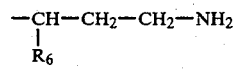

8. The epoxy resin composition of claim 7, wherein $R_6$ is H.

9. In a method for curing an epoxy resin composition comprising incorporating an epoxy resin curing agent into an epoxy resin and heating the combination of the epoxy resin and the epoxy during agent, the improvement which comprises said epoxy resin curing agent being represented by the formula:

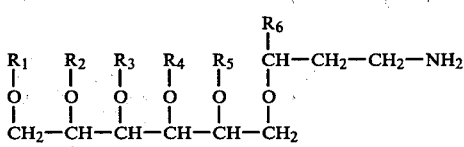

wherein $R_1$, $R_2$, $R_3$, $R_4$, and $R_5$ are independently selected from H and

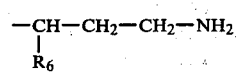

wherein $R_6$ is selected from H and a lower alkyl group having from 1 to about 4 carbon atoms.

* * * * *